(12) United States Patent
Hanna et al.

(10) Patent No.: US 9,340,565 B2
(45) Date of Patent: May 17, 2016

(54) CRYSTALLINE FORMS

(75) Inventors: Mazen Hanna, Lutz, FL (US); Ning Shan, Tampa, FL (US); Miranda L. Cheney, Tampa, FL (US); David R. Weyna, Tampa, FL (US); Paul K. Isbester, Castleton, NY (US); Xufeng Sun, Schenectady, NY (US)

(73) Assignee: THAR PHARMACEUTICALS, INC., Pittsburg, PA (US)

( * ) Notice: Subject to any disclaimer, the term of this patent is extended or adjusted under 35 U.S.C. 154(b) by 387 days.

(21) Appl. No.: 13/989,394

(22) PCT Filed: Nov. 23, 2011

(86) PCT No.: PCT/US2011/062050
§ 371 (c)(1),
(2), (4) Date: Aug. 12, 2013

(87) PCT Pub. No.: WO2012/071517
PCT Pub. Date: May 31, 2012

(65) Prior Publication Data

US 2013/0316982 A1    Nov. 28, 2013

Related U.S. Application Data

(60) Provisional application No. 61/458,514, filed on Nov. 24, 2010.

(51) Int. Cl.
*C07F 9/6506* (2006.01)
*C07C 225/06* (2006.01)
*A61K 31/675* (2006.01)

(52) U.S. Cl.
CPC ......... *C07F 9/65061* (2013.01); *A61K 31/675* (2013.01); *C07C 225/06* (2013.01)

(58) Field of Classification Search
CPC .. C07F 9/65061; C07C 225/06; A61K 31/675
See application file for complete search history.

(56) References Cited

U.S. PATENT DOCUMENTS

| | | | |
|---|---|---|---|
| 3,959,361 A | 5/1976 | Krueger et al. | |
| 3,961,934 A | 6/1976 | Ratts | |
| 4,939,130 A | 7/1990 | Jaeggi et al. | |
| 5,431,920 A | 7/1995 | Bechard | |
| 5,512,552 A | 4/1996 | Sohda et al. | |
| 6,468,559 B1 | 10/2002 | Chen et al. | |
| 6,476,006 B2 | 11/2002 | Flashner-Barak et al. | |
| 6,541,454 B1 | 4/2003 | Breuer et al. | |
| 6,676,965 B1 | 1/2004 | Lulla et al. | |
| 6,676,970 B2 | 1/2004 | Bader et al. | |
| 6,677,320 B2 | 1/2004 | Diederich et al. | |
| 6,936,275 B2 | 8/2005 | Fassihi et al. | |
| 7,008,640 B2 | 3/2006 | Watanabe et al. | |
| 7,011,847 B2 | 3/2006 | Lulla et al. | |
| 7,038,083 B2 | 5/2006 | Lidor-Hadas et al. | |
| 7,192,938 B2 | 3/2007 | Bauss et al. | |
| 7,309,698 B2 | 12/2007 | Boyd et al. | |
| 7,332,603 B2 | 2/2008 | De Ferra et al. | |
| 7,345,088 B2 | 3/2008 | Green et al. | |
| 7,354,912 B2 | 4/2008 | Lichtenberger et al. | |
| 7,410,957 B2 | 8/2008 | Bauss et al. | |
| 7,411,087 B2 | 8/2008 | Patel et al. | |
| 7,425,549 B2 | 9/2008 | Little et al. | |
| 7,435,827 B2 | 10/2008 | Aronhime et al. | |
| 7,439,385 B2 | 10/2008 | Deshpande et al. | |
| 7,473,684 B2 | 1/2009 | Harrison et al. | |
| 7,528,280 B2 | 5/2009 | Danda et al. | |
| 7,582,768 B2 | 9/2009 | Aronhime et al. | |
| 7,589,211 B2 | 9/2009 | Aronhime et al. | |
| 7,645,459 B2 | 1/2010 | Dansereau et al. | |
| 7,645,460 B2 | 1/2010 | Dansereau et al. | |
| 7,687,636 B2 | 3/2010 | Aronhime et al. | |
| 7,704,977 B2 | 4/2010 | Leonard | |
| 7,718,634 B2 | 5/2010 | Bauss et al. | |
| 7,820,722 B2 | 10/2010 | Raoof et al. | |
| 8,053,429 B2 | 11/2011 | Cumming et al. | |
| 8,119,159 B2 | 2/2012 | Cumming et al. | |
| 8,158,153 B2 | 4/2012 | Liversidge et al. | |
| 8,399,023 B2 | 3/2013 | Hanna et al. | |
| 2001/0053388 A1 | 12/2001 | Bader et al. | |
| 2002/0142996 A1 | 10/2002 | Okuno et al. | |
| 2003/0064966 A1 | 4/2003 | Palepu | |
| 2003/0091623 A1 | 5/2003 | Cumming et al. | |
| 2003/0181421 A1 | 9/2003 | Horowitz et al. | |
| 2004/0047835 A1 | 3/2004 | Bianco | |
| 2004/0127466 A1 | 7/2004 | Palepu | |
| 2004/0147484 A1 | 7/2004 | Boyd et al. | |
| 2004/0157798 A1 | 8/2004 | Little | |
| 2004/0157799 A1 | 8/2004 | Seaman | |
| 2004/0176327 A1 | 9/2004 | Okuno et al. | |
| 2004/0220264 A1 | 11/2004 | Yu et al. | |
| 2004/0230076 A1 | 11/2004 | Lifshitz-Liron et al. | |
| 2005/0054616 A1 | 3/2005 | Aronhime et al. | |
| 2005/0065117 A1 | 3/2005 | Lee | |
| 2005/0260262 A1 | 11/2005 | Dansereau et al. | |
| 2006/0068010 A1 | 3/2006 | Turner et al. | |
| 2006/0069069 A1 | 3/2006 | Kajander et al. | |
| 2006/0134190 A1 | 6/2006 | Kim et al. | |

(Continued)

FOREIGN PATENT DOCUMENTS

AR 80072 3/2012
AU 2010278860 A1 2/2011

(Continued)

OTHER PUBLICATIONS

Office Action for Japanese Application No. 2012-523084 dated Aug. 1, 2014.

(Continued)

*Primary Examiner* — Joseph Kosack
(74) *Attorney, Agent, or Firm* — J.A. Lindeman & Co., PLLC

(57) ABSTRACT

Preparation and characterization of novel forms of (1-hydroxy-2-imidazol-1-yl-1-phosphono-ethyl) phosphonic acid, suitable for pharmaceutical compositions in drug delivery systems for humans.

20 Claims, 2 Drawing Sheets

(56) References Cited

U.S. PATENT DOCUMENTS

| | | |
|---|---|---|
| 2006/0173009 A1 | 8/2006 | Kanoh et al. |
| 2006/0178439 A1 | 8/2006 | Mohakhud et al. |
| 2006/0210639 A1 | 9/2006 | Liversidge |
| 2007/0015736 A1 | 1/2007 | Glausch et al. |
| 2007/0021616 A1 | 1/2007 | Aronhime et al. |
| 2007/0021617 A1 | 1/2007 | Aronhime et al. |
| 2007/0021618 A1 | 1/2007 | Aronhime et al. |
| 2007/0021619 A1 | 1/2007 | Aronhime et al. |
| 2007/0049557 A1 | 3/2007 | Ahmed et al. |
| 2007/0088161 A1 | 4/2007 | Stockel et al. |
| 2007/0134319 A1 | 6/2007 | Zannou et al. |
| 2007/0196464 A1 | 8/2007 | Cumming et al. |
| 2007/0218130 A1 | 9/2007 | Ahmed et al. |
| 2007/0225258 A1 | 9/2007 | Walsh |
| 2007/0238707 A1 | 10/2007 | Leonard |
| 2008/0090784 A1 | 4/2008 | Labriola et al. |
| 2008/0139514 A1 | 6/2008 | Gore et al. |
| 2008/0153784 A1 | 6/2008 | Zhang et al. |
| 2008/0153785 A1 | 6/2008 | Shin et al. |
| 2008/0167271 A1 | 7/2008 | Masini-Eteve |
| 2008/0249069 A1 | 10/2008 | Bauss et al. |
| 2008/0254089 A1 | 10/2008 | Glausch et al. |
| 2008/0255366 A1 | 10/2008 | Mohakhud et al. |
| 2008/0275001 A1 | 11/2008 | Cumming et al. |
| 2008/0286359 A1 | 11/2008 | Dansereau et al. |
| 2008/0287400 A1 | 11/2008 | Dansereau et al. |
| 2009/0023683 A1 | 1/2009 | Kocherlakota et al. |
| 2009/0075941 A1 | 3/2009 | Selander et al. |
| 2009/0082312 A1 | 3/2009 | Czamik |
| 2009/0137808 A1 | 5/2009 | Samsel et al. |
| 2009/0209763 A1 | 8/2009 | Lidor-Hadas et al. |
| 2009/0215729 A1 | 8/2009 | Johnson et al. |
| 2009/0238876 A1 | 9/2009 | Danenberg et al. |
| 2009/0281064 A1 | 11/2009 | Ahmed et al. |
| 2010/0029596 A1 | 2/2010 | Ryu et al. |
| 2010/0047306 A1 | 2/2010 | Loeffler et al. |
| 2010/0056481 A1 | 3/2010 | Glausch et al. |
| 2010/0086593 A1 | 4/2010 | Dansereau et al. |
| 2010/0113394 A1 | 5/2010 | Dansereau et al. |
| 2010/0113395 A1 | 5/2010 | Dansereau et al. |
| 2010/0119559 A1 | 5/2010 | Dansereau et al. |
| 2010/0215743 A1 | 8/2010 | Leonard |
| 2010/0248640 A1 | 9/2010 | Machaughtan et al. |
| 2011/0028435 A1* | 2/2011 | Hanna et al. ............ 514/89 |
| 2011/0182985 A1 | 7/2011 | Coughlan et al. |
| 2011/0263537 A1 | 10/2011 | Desai |

FOREIGN PATENT DOCUMENTS

| | | |
|---|---|---|
| AU | 2011218625 A1 | 9/2011 |
| CN | 102070668 | 7/2013 |
| CN | 103070668 | 7/2013 |
| EP | 1154761 A1 | 11/2001 |
| EP | 1392325 A1 | 3/2004 |
| EP | 1567533 A2 | 8/2005 |
| EP | 1591122 A1 | 11/2005 |
| EP | 1612212 A1 | 1/2006 |
| EP | 1880744 A1 | 1/2008 |
| EP | 1925621 A1 | 5/2008 |
| JP | 2003-520240 | 7/2003 |
| JP | 2004-528303 A | 9/2004 |
| JP | 2008-533173 A | 8/2008 |
| WO | 92/14474 A1 | 9/1992 |
| WO | 95/08331 A1 | 3/1995 |
| WO | 96/07417 A1 | 3/1996 |
| WO | 97/05903 A2 | 2/1997 |
| WO | 98/52547 A1 | 11/1998 |
| WO | 98/56360 A2 | 12/1998 |
| WO | 00/21541 A1 | 4/2000 |
| WO | 00/50012 A1 | 8/2000 |
| WO | 00/61111 | 10/2000 |
| WO | 00/64516 A1 | 11/2000 |
| WO | 01/52859 A1 | 7/2001 |
| WO | 01/82903 A1 | 11/2001 |
| WO | 01/97788 A2 | 12/2001 |
| WO | 02/080933 A1 | 10/2002 |
| WO | 02/087554 A2 | 11/2002 |
| WO | 02/089816 A1 | 11/2002 |
| WO | 03/007916 A1 | 1/2003 |
| WO | 03/051373 A1 | 6/2003 |
| WO | 2004/024165 A1 | 3/2004 |
| WO | 2004/035061 A1 | 4/2004 |
| WO | 2004/056373 A1 | 7/2004 |
| WO | 2004/075860 A2 | 9/2004 |
| WO | 2004/078161 A1 | 9/2004 |
| WO | 2004/078163 A2 | 9/2004 |
| WO | 2004/100941 A1 | 11/2004 |
| WO | 2005/000404 A2 | 1/2005 |
| WO | 2005/005447 A2 | 1/2005 |
| WO | 2005/025551 A2 | 3/2005 |
| WO | 2005/037157 A1 | 4/2005 |
| WO | 2005/044831 A2 | 5/2005 |
| WO | 2005/048979 A2 | 6/2005 |
| WO | 2005/063218 A2 | 7/2005 |
| WO | 2005/063717 A1 | 7/2005 |
| WO | 2005/099676 A2 | 10/2005 |
| WO | 2005/115331 A2 | 12/2005 |
| WO | 2006/018033 A1 | 2/2006 |
| WO | 2006/019843 A1 | 2/2006 |
| WO | 2006/020009 A1 | 2/2006 |
| WO | 2006/039499 A2 | 4/2006 |
| WO | 2006/066067 A2 | 6/2006 |
| WO | 2006/080780 A1 | 8/2006 |
| WO | 2006/102117 A1 | 9/2006 |
| WO | 2006/112889 A1 | 10/2006 |
| WO | 2007/016982 A1 | 2/2007 |
| WO | 2007/023342 A2 | 3/2007 |
| WO | 2007/032808 A1 | 3/2007 |
| WO | 2007/069049 A2 | 6/2007 |
| WO | 2007/093226 A1 | 8/2007 |
| WO | 2007/117706 A2 | 10/2007 |
| WO | 2007/125521 A2 | 11/2007 |
| WO | 2007/146234 A2 | 12/2007 |
| WO | 2008/040763 A1 | 4/2008 |
| WO | 2008/058722 A1 | 5/2008 |
| WO | 2008/064849 A1 | 6/2008 |
| WO | 2008/085281 A1 | 7/2008 |
| WO | 2008/100767 A1 | 8/2008 |
| WO | 2008/113177 A1 | 9/2008 |
| WO | 2009/018834 A1 | 2/2009 |
| WO | 2009/035265 A2 | 3/2009 |
| WO | 2009/040818 A1 | 4/2009 |
| WO | 2009/042179 A1 | 4/2009 |
| WO | 2009/056952 A1 | 5/2009 |
| WO | 2009/068567 A1 | 6/2009 |
| WO | 2009/072119 A2 | 6/2009 |
| WO | 2009/107850 A1 | 9/2009 |
| WO | 2009/112493 A1 | 9/2009 |
| WO | 2009/121935 A2 | 10/2009 |
| WO | 2010/014765 A1 | 2/2010 |
| WO | 2010/014766 A1 | 2/2010 |
| WO | 2010/060619 A1 | 6/2010 |
| WO | 2010/071866 A2 | 6/2010 |
| WO | 2010/099255 A1 | 9/2010 |
| WO | 2011014781 A1 | 2/2011 |
| WO | 2011/097269 A9 | 8/2011 |
| WO | 2011097269 A1 | 8/2011 |
| WO | 2011/132826 A1 | 10/2011 |
| WO | 2012/071517 A2 | 5/2012 |

OTHER PUBLICATIONS

Patent Examination Report in Australian Application No. 2010278860 dated Aug. 14, 2014.

Patent Examination Report in AU Application No. 2012216632 dated Aug. 14, 2014.

International Preliminary Report on Patentability in PCT application No. PCT/US2011/062050 dated Mar. 6, 2014.

Atelvia Prescribing Information.

International Preliminary Report on Patentability in PCT application No. PCT/US2011/023427 dated Aug. 7, 2012.

International Preliminary Report on Patentability in PCT application No. PCT/US2010/043892 dated Feb. 9, 2012.

(56) References Cited

OTHER PUBLICATIONS

Written Opinion of the International Searching Authority of PCT International Application No. PCT/US2020/043892, dated Feb. 11, 2011.
Wasserman et al., "The Influence of Amino Acids and Other Organic Compounds on the Gastrointestinal Absorption of Calcium and Strontium in the Rat," J. Nutr. 371-383 (1956).
Gueguen et al., "The Bioavailability of Dietary Calcium," J. Am. Col. Nutr. 19(2):119S-136S (2000).
Dupuis et al., "Enterocyte Microvillus Can Phosphorylate Molecules Which Inhibit Endogenous Phosphorylation of its Proteins," Archives Internationales de Physiologie et de Biochimie 92:1-11 (1984).
Dupuis et al., "Does the Inihbition of Microvillus Protein Phosphorylation by Lysine Explain the Activity of the Latter on Calcium Transfer?" J. Biochem. 13:1163-1170 (1981).
Bronner, "Current Concepts of Calcium Absorption: An Overview," J. Nutr. 122:642-643 (1992).
Bronner, "Intestinal Calcium Absorption: Mechanisms and Applications," J. Nutr. 1347-1352 (1987).
International Search Report and Written Opinion for PCT International Application No. PCT/US2010/043916, dated Sep. 27, 2010.
McNamara et al., "Use of a Glutaric Acid Cocrystal to Improve Oral Bioavailability of a Low Solubility API," Pharmaceutical Research 23(8):1888-1897 (2006).
International Search Report and Written Opinion of PCT PCT/US11/23427 dated Apr. 22, 2011.
PCT International Search Report of PCT International Application No. PCT/US2010/043892, dated Feb. 11, 2011.
European Search Report for PCT/US2010/043916 dated Jan. 15, 2013.
Supplemental European Search Report for PCT/US2011/023427, dated Dec. 10, 2013.
Office Action for JP Application No. 2012-552048 dated Sep. 17, 2014.
International Search Report in PCT application No. PCT/US2011/023427 dated Aug. 11, 2011.
Office Action in U.S. Appl. No. 13/567,827 dated Jul. 15, 2014.
J. Ulrich, "Crystallization," Kirk-Othmer Encyclopedia of Chemical Technology, Aug. 16, 2012.
S. Vippagunta et al., "Crystalline Solids," Advanced Drug Delivery Review, vol. 48, pp. 3-26, 2001.
PCT International Search Report and Written Opinion of PCT International Application No. PCT/US2011/062050, dated Apr. 10, 2012.
Coleman et al., "The effects of adding zoledronic acid to neoadjuvant chemotherapy on tumour response: exploratory evidence for direct anti-tumour activity in breast cancer," British J Cancer 102(7):1099-1105 (2010).
Davies et al., "Evaluating the effects of zoledronic acid (ZOL) on overall survival (OS) in patients (Pts) with multiple myeloma (MM): Results of the Medical Research Council (MRC) Myeloma IX study," J Clinical Oncology 28(15): Abstract 8021 (2010).
Gnant et al., "Endocrine Therapy plus Zoledronic Acid in Premenopausal Breast Cancer," New England J Medicine 360(17):679-691 (2009).
Sorbera et al., "Zoledronate Disodium. Treatment of tumor-induced hypercalcemia, Angiogenesis inhibitor," Drugs of the Future 25(3):259-268 (2000).

* cited by examiner

CRYSTALLINE FORMS

CROSS REFERENCE TO RELATED APPLICATIONS

This application claims priority to U.S. Provisional Application 61/458,514, filed 24 Nov. 2010, incorporated by reference in its entirety.

FIELD OF THE INVENTION

This disclosure pertains to generating novel crystalline forms of (1-hydroxy-2-imidazol-1-yl-1-phosphono-ethyl) phosphonic acid, in which such forms include but are not limited to cocrystals, salts, hydrates, solvates, solvates of salts, and mixtures thereof. Methods for the preparation and pharmaceutical compositions suitable for drug delivery systems that include one or more of these new forms are disclosed.

BACKGROUND OF THE INVENTION

Zoledronic acid, known as (1-hydroxy-2-imidazol-1-yl-1-phosphono-ethyl)phosphonic acid, is depicted by the following chemical structure:

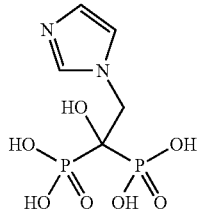

Zoledronic acid is a third generation bisphosphonate which far exceeds the previous generations in terms of efficacy and is used predominately for indications of osteoporosis, Paget's disease, hypercalcemia, and inhibition of bone metastasis. It was originally developed by Novartis and marketed as the monohydrate under the brand names Zometa® and Reclast®. Zoledronic acid was first approved in 2000 for the treatment of hypercalcemia in Canada. It was later approved for use in the US for hypercalcemia in 2001, for multiple myeloma and bone metastases from solid tumors in 2002, and for osteoporosis and Paget's disease in 2007. Clinical trials have also been conducted or are on-going exploring the use of zoledronic acid in neoadjuvant or adjuvant cancer therapy, Coleman, et al., British J Cancer 2010;102(7):1099-1105, Gnant, et al., New England J Medicine. 2009, 360 (17):679-691 and Davies, et al. J Clinical Oncology, 2010, 28(7s): Abstract 8021. Zoledronic acid is administered as an intravenous (IV) dose of 4 mg over 15 minutes per month for hypercalcemia of malignancy, multiple myeloma, and bone metastases from solid tumors, while an IV dose of 5 mg over 15 minutes is used for osteoporosis and Paget's disease. Zoledronic acid is sparingly soluble in water and 0.1 N HCl solution but is freely soluble in 0.1 N NaOH. Zoledronic acid is practically insoluble in various organic solvents. Much effort has been taken to generate novel oral formulations of zoledronic acid through crystallization and metal salt formation to improve its aqueous solubility, permeability, and subsequent oral bioavailability. A crystalline trihydrate was disclosed in the U.S. Patent application 2006/0178439 A1 and world patent application WO2007/032808. Seven hydrated forms, an amorphous form, three monosodium salts, and eleven disodium salts with varying degrees of hydration of zoledronic acid were also disclosed in the patent application WO2005/005447 A2. Zoledronate metal salts including $Na^+$, $Mg^{2+}$, $Zn^{2+}$ were reported in the journal of Drugs of the Future (Sorbera et al, 25(3), *Drugs of the Future*, (2000)). Zoledronate, zoledronic, or zoledronic salt represents the ionic form of zoledronic acid. Patent application WO2008/064849 A1 from Novartis disclosed additional metal salts including two $Ca^{2+}$ salts, two $Zn^{2+}$ salts, one $Mg^{2+}$ salt, as well as a monohydrate, a trihydrate, an amorphous form, and an anhydrous form.

According to the US Food and Drug Administration (FDA) Summary Basis of Approval (SBA) for zoledronic acid, the poor oral bioavailability (approximately 1%), is partially due to its poor permeability in the GI tract. It was also noted that insoluble metal complexes were formed in the upper intestines, most commonly with calcium. Zoledronic acid has also been shown to cause severe gastric and intestinal irritations. In some cases the irritations were so severe that medical treatment was required.

Due to the fact that zoledronic acid is only available as a parenteral dosage form there is a clear need to develop novel forms of zoledronic acid that can be included in an oral dosage form particularly as the use of orally administered drugs are becoming more wide spread in many therapeutic areas including the treatment of cancer. The upward trend in the use of oral drugs will continue especially in light of the goal to decrease the overall cost of healthcare. Thus, there is an opportunity to create oral dosage forms of IV drugs where oral dosage forms do not yet exist due to their poor aqueous solubility and/or poor permeability providing a clear clinical benefit for patients.

Recent activity concerning the development of oral formulations has led to the use of medium chain fatty acids to enhance the drug's low permeability as disclosed in the US 2007/0134319 A1 and US 2007/0196464 patent applications. Modified amino acid carriers, but not pure proteinogenic amino acids, have also been employed to improve the absorption of the drug as shown in the WO 2007/093226 A1 application.

The development of oral forms of zoledronic acid has been problematic due to its poor aqueous solubility and permeability. By using pharmaceutically acceptable cocrystal formers to bond with pure zoledronic acid to create novel molecular complexes neutral and ionic (e.g. cocrystals, salts and solvates) which can improve solubility and/or permeability, the opportunity is therefore provided to tackle such problems and develop an oral dosage form.

All of the above attempts to improve the oral bioavailability of zoledronic acid were either focused on improving the aqueous solubility by generating novel solid forms, or by mixing the drug with an inactive ingredient that has enhanced GI tract permeability. The improvement of aqueous solubility failed to improve the bioavailability of zoledronic acid, since the formation of insoluble zoledronate calcium complexes is unlikely to be prevented. On the other hand, powder mixtures of the poorly permeable drug with inactive permeability enhancers improved the bioavailability of the drug. This approach of mixing different materials with different particle sizes and size distributions could result in poor blend/physical mixture uniformity. Constituents of the mixture could also segregate during transportation or with shaking and vibration.

Additionally, the powder blends require that the ingredients are compatible and no potential for solid-solid interaction with or without atmospheric interferences exist thus impacting on their physical stability during storage or in a delivery system.

To the best of the inventors' knowledge, no attempt has been made prior to this invention towards a deliberate molecular design to create a molecular complex of the drug and additional component(s) (coformer(s)) in a single crystalline structure that is physically stable and is not influenced by the addition of excess coformer(s) in the formulation. The benefit of such design can lead to the elimination of all potential physical instability in the physical mix of the molecular complex and the coformer(s). Additionally, the resulting molecular complexes possess very different physicochemical properties compared to the parent drug, coformer or their physical mixture. These properties include but are not limited to melting point, thermal and electrical conductivity, aqueous solubility, rate of dissolution and permeability across the GI tract membrane.

Orally administered drugs are becoming more preferred in various therapeutic areas including cancers. Clearly, there is an opportunity to create oral dosage forms of IV drugs where oral dosage forms do not yet exist due to their poor aqueous solubility and/or poor permeability providing a clear clinical benefit for patients. Given the fact that zoledronic acid is only approved for IV administration, there is a need to develop an oral dosage form of zoledronic acid. By using pharmaceutically acceptable and/or approved coformers to hydrogen bond with zoledronic acid, novel molecular complexes (e.g. cocrystals, salts, solvates, and mixtures thereof) with improve solubility and/or permeability can be created. These novel molecular complexes could be used in the development of an oral dosage form for zoledronic acid.

SUMMARY OF THE INVENTION

The present disclosure is directed towards generating new forms of zoledronic acid, which have the therapeutic efficacy of zoledronic acid discussed above, with improved aqueous solubility, rate of dissolution, and/or improved permeability and thus enhanced bioavailability. One aspect of the present disclosure includes novel molecular complexes of zoledronic acid that includes cocrystals, salts, and solvates (e.g. hydrates and mixed solvates as well as solvates of salts), and mixtures containing such materials. In addition, the disclosure further includes methods for the preparation of such complexes.

The disclosure further includes compositions of molecular complexes of zoledronic acid suitable for incorporation in a pharmaceutical dosage form. Specific molecular complexes pertaining to the disclosure include, but are not limited to, complexes of zoledronic acid, DL-lysine. Obvious variants of the disclosed zoledronic acid forms in the disclosure, including those described by the drawings and examples, will be readily apparent to the person of ordinary skill in the art having the present disclosure and such variants are considered to be a part of the current invention.

In one aspect the invention provides for a crystalline form of zoledronic acid: DL-lysine.

In one embodiment the crystalline form is characterized by a powder X-ray diffraction pattern comprising a powder X-ray diffraction peak at about 6.6±0.2 degrees 2-theta.

In one embodiment the crystalline form is characterized by a powder X-ray diffraction pattern comprising a powder X-ray diffraction peak at about 11.0±0.2 degrees 2-theta.

In one embodiment the crystalline form is characterized by a powder X-ray diffraction pattern comprising a powder X-ray diffraction peak at about 14.2±0.2 degrees 2-theta.

In one embodiment the crystalline form is characterized by a powder X-ray diffraction pattern comprising a powder X-ray diffraction peak at about 18.3±0.2 degrees 2-theta.

In one embodiment the crystalline form is characterized by a powder X-ray diffraction pattern comprising a powder X-ray diffraction peak at about 19.7±0.2 degrees 2-theta.

In one embodiment the crystalline form is characterized by a powder X-ray diffraction pattern comprising a powder X-ray diffraction peak at about 22.7±0.2 degrees 2-theta.

In one embodiment the crystalline form is characterized by a powder X-ray diffraction pattern comprising a powder X-ray diffraction peak at about 27.6±0.2 degrees 2-theta.

In one embodiment the crystalline form is characterized by a powder X-ray diffraction pattern comprising powder X-ray diffraction peaks at about 6.6 and 18.3±0.2 degrees 2-theta.

In one embodiment the crystalline form is characterized by a powder X-ray diffraction pattern comprising powder X-ray diffraction peaks at about 6.6 and 19.7±0.2 degrees 2-theta.

In one embodiment the crystalline form is characterized by a powder X-ray diffraction pattern comprising powder X-ray diffraction peaks at about 6.6 and 22.7±0.2 degrees 2-theta.

In one embodiment the crystalline form is characterized by a powder X-ray diffraction pattern comprising powder X-ray diffraction peaks at about 6.6, 18.3 and 19.7±0.2 degrees 2-theta.

In one embodiment the crystalline form is characterized by a powder X-ray diffraction pattern comprising powder X-ray diffraction peaks at about 18.3 and 19.7±0.2 degrees 2-theta.

In one embodiment the crystalline form is characterized by a powder X-ray diffraction pattern comprising powder X-ray diffraction peaks at about 18.3, 19.7 and 27.6±0.2 degrees 2-theta.

In one embodiment the crystalline form is characterized by a powder X-ray diffraction pattern comprising powder X-ray diffraction peaks at about 18.3 and 22.7±0.2 degrees 2-theta.

In one embodiment the crystalline form is characterized by a powder X-ray diffraction pattern comprising powder X-ray diffraction peaks at about 6.6, 18.3 and 22.7±0.2 degrees 2-theta.

In one embodiment the crystalline form is characterized by a powder X-ray diffraction pattern comprising powder X-ray diffraction peaks at about 19.7 and 22.7±0.2 degrees 2-theta.

In one embodiment the crystalline form is characterized by a powder X-ray diffraction pattern comprising powder X-ray diffraction peaks at about 19.7, 22.7 and 27.6±0.2 degrees 2-theta.

In one embodiment the crystalline form is characterized by a powder X-ray diffraction pattern comprising powder X-ray diffraction peaks at about 6.6, 19.7 and 22.7±0.2 degrees 2-theta.

In one embodiment the crystalline form is characterized by a powder X-ray diffraction pattern comprising powder X-ray diffraction peaks at about 18.3, 19.7 and 22.7±0.2 degrees 2-theta.

In one embodiment the crystalline form is characterized by a powder X-ray diffraction pattern comprising powder X-ray diffraction peaks at about 6.6, 18.3, 19.7 and 22.7±0.2 degrees 2-theta.

In one embodiment the crystalline form is characterized by a powder X-ray diffraction pattern comprising powder X-ray diffraction peaks at about 14.2, 18.3, 19.7 and 22.7±0.2 degrees 2-theta.

In one embodiment the crystalline form is characterized by a powder X-ray diffraction pattern comprising powder X-ray diffraction peaks at about 6.6, 14.2, 18.3, 19.7 and 22.7±0.2 degrees 2-theta.

In one embodiment the crystalline form is characterized by a powder X-ray diffraction pattern comprising powder X-ray diffraction peaks at about 6.6, 14.2, 18.3, 19.7, 22.7 and 27.6±0.2 degrees 2-theta.

In one embodiment the crystalline form is characterized by a powder X-ray diffraction pattern comprising powder X-ray diffraction peaks at about 6.6, 11.0, 14.2, 18.3, 19.7, 22.7 and 27.6±0.2 degrees 2-theta.

In one embodiment the crystalline form is characterized by a powder X-ray diffraction pattern comprising a powder X-ray diffraction peak at about 7.2±0.2 degrees 2-theta.

In one embodiment the crystalline form is characterized by a powder X-ray diffraction pattern comprising a powder X-ray diffraction peak at about 14.0±0.2 degrees 2-theta.

In one embodiment the crystalline form is characterized by a powder X-ray diffraction pattern comprising a powder X-ray diffraction peak at about 18.3±0.2 degrees 2-theta.

In one embodiment the crystalline form is characterized by a powder X-ray diffraction pattern comprising a powder X-ray diffraction peak at about 19.1±0.2 degrees 2-theta.

In one embodiment the crystalline form is characterized by a powder X-ray diffraction pattern comprising a powder X-ray diffraction peak at about 20.7±0.2 degrees 2-theta.

In one embodiment the crystalline form is characterized by a powder X-ray diffraction pattern comprising a powder X-ray diffraction peak at about 24.6±0.2 degrees 2-theta.

In one embodiment the crystalline form is characterized by a powder X-ray diffraction pattern comprising a powder X-ray diffraction peak at about 34.4±0.2 degrees 2-theta.

In one embodiment the crystalline form is characterized by a powder X-ray diffraction pattern comprising powder X-ray diffraction peaks at about 7.2 and 18.3±0.2 degrees 2-theta.

In one embodiment the crystalline form is characterized by a powder X-ray diffraction pattern comprising powder X-ray diffraction peaks at about 7.2 and 19.1±0.2 degrees 2-theta.

In one embodiment the crystalline form is characterized by a powder X-ray diffraction pattern comprising powder X-ray diffraction peaks at about 7.2 and 20.7±0.2 degrees 2-theta.

In one embodiment the crystalline form is characterized by a powder X-ray diffraction pattern comprising powder X-ray diffraction peaks at about 7.2, 18.3 and 19.1±0.2 degrees 2-theta.

In one embodiment the crystalline form is characterized by a powder X-ray diffraction pattern comprising powder X-ray diffraction peaks at about 18.3 and 19.1±0.2 degrees 2-theta.

In one embodiment the crystalline form is characterized by a powder X-ray diffraction pattern comprising powder X-ray diffraction peaks at about 18.3, 19.1 and 24.6±0.2 degrees 2-theta.

In one embodiment the crystalline form is characterized by a powder X-ray diffraction pattern comprising powder X-ray diffraction peaks at about 18.3 and 20.7±0.2 degrees 2-theta.

In one embodiment the crystalline form is characterized by a powder X-ray diffraction pattern comprising powder X-ray diffraction peaks at about 7.2, 18.3 and 20.7±0.2 degrees 2-theta.

In one embodiment the crystalline form is characterized by a powder X-ray diffraction pattern comprising powder X-ray diffraction peaks at about 19.1 and 20.7±0.2 degrees 2-theta.

In one embodiment the crystalline form is characterized by a powder X-ray diffraction pattern comprising powder X-ray diffraction peaks at about 19.1, 20.7 and 24.6±0.2 degrees 2-theta.

In one embodiment the crystalline form is characterized by a powder X-ray diffraction pattern comprising powder X-ray diffraction peaks at about 7.2, 19.1 and 20.7±0.2 degrees 2-theta.

In one embodiment the crystalline form is characterized by a powder X-ray diffraction pattern comprising powder X-ray diffraction peaks at about 18.3, 19.1 and 20.7±0.2 degrees 2-theta.

In one embodiment the crystalline form is characterized by a powder X-ray diffraction pattern comprising powder X-ray diffraction peaks at about 7.2, 18.3, 19.1 and 20.7±0.2 degrees 2-theta.

In one embodiment the crystalline form is characterized by a powder X-ray diffraction pattern comprising powder X-ray diffraction peaks at about 14.0, 18.3, 19.1 and 20.7±0.2 degrees 2-theta.

In one embodiment the crystalline form is characterized by a powder X-ray diffraction pattern comprising powder X-ray diffraction peaks at about 7.2, 14.0, 18.3, 19.1 and 20.7±0.2 degrees 2-theta.

In one embodiment the crystalline form is characterized by a powder X-ray diffraction pattern comprising powder X-ray diffraction peaks at about 7.2, 14.0, 18.3, 19.1, 20.7 and 24.6±0.2 degrees 2-theta.

In one embodiment the crystalline form is characterized by a powder X-ray diffraction pattern comprising powder X-ray diffraction peaks at about 7.2, 14.0, 18.3, 19.1, 20.7, 24.6 and 34.4±0.2 degrees 2-theta.

The foregoing and other features and advantages of the disclosed technology will become more apparent from the following detailed description, which proceeds with reference to the accompanying drawings. Such description is meant to be illustrative, but not limiting, of the invention.

DETAILED DESCRIPTION OF THE PREFERRED EMBODIMENTS

Figure 1:
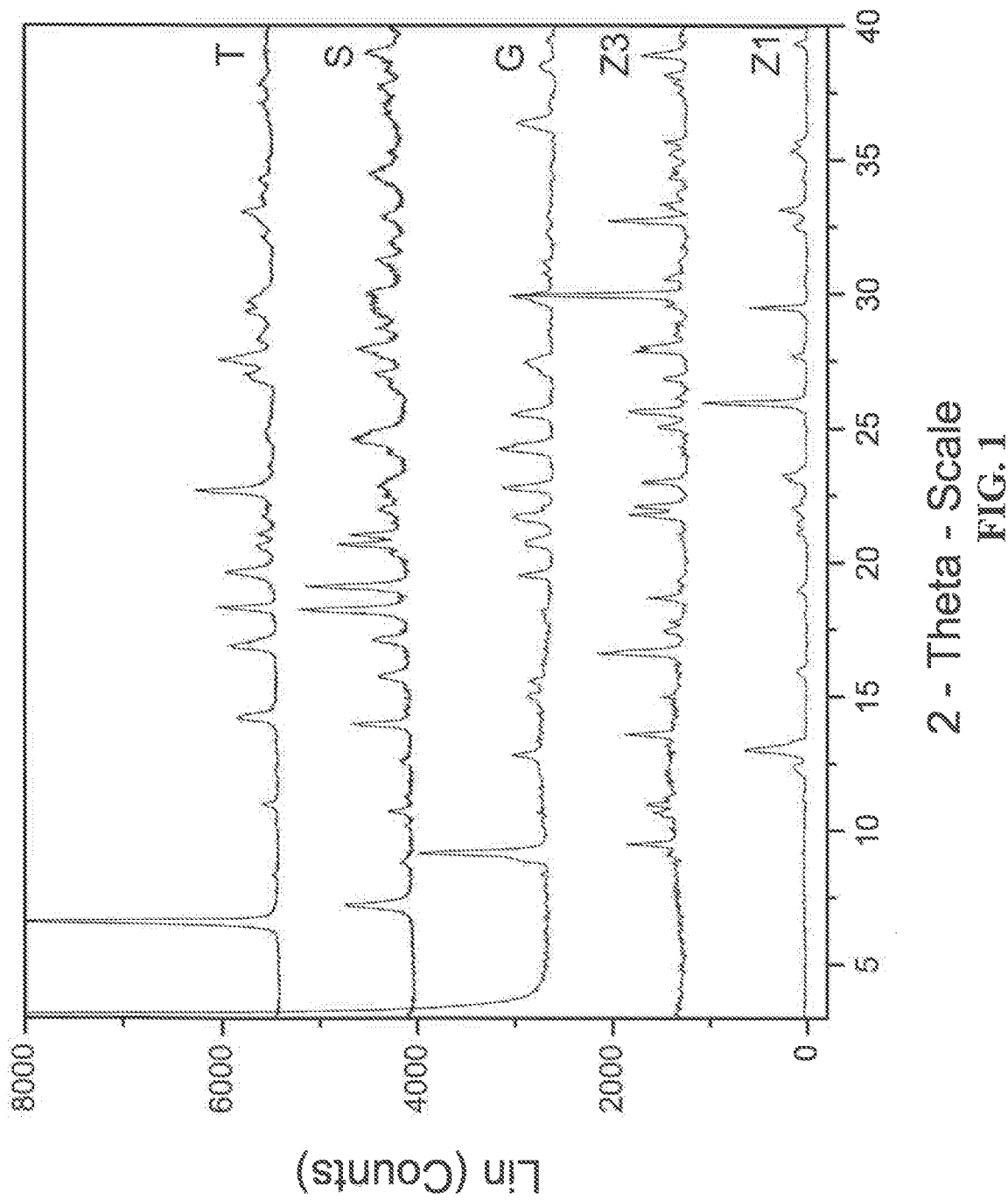
FIG. 1 PXRD diffractograms of: (T=zoledronic:DL-lysine complex, S=zoledronic:DL-lysine complex,), (G=DL-lysine), (Z1=Zoledronic acid monohydrate), and (Z3=Zoledronic acid trihydrate).

In general, active pharmaceutical ingredients (APIs) in the pharmaceutical compositions can be prepared in a variety of different forms including prodrugs, amorphous forms, solvates, hydrates, cocrystals, salts and polymorphs. The discovery of novel API forms may provide an opportunity to improve the performance characteristics of a pharmaceutical product. Additionally, discovery of novel drug forms expands the array of resources available for designing pharmaceutical dosage forms with targeted release profiles or other desired characteristics.

A specific characteristic that can be targeted includes the novel crystal form of an API and its subsequent new physicochemical properties. The alteration of the crystal form of a given API could result in the modification of the physical properties of the target molecule. For example, various polymorphs of a given API exhibit different aqueous solubility where the thermodynamically stable polymorph would exhibit a lower solubility than the meta-stable polymorph. In addition, pharmaceutical polymorphs can also differ in properties such as rate of dissolution, shelf life, bioavailability, morphology, vapor pressure, density, color, and compressibility. Accordingly, it is desirable to enhance the properties of an API by forming molecular complexes such as a cocrystal, salt, solvate or hydrate with respect to aqueous solubility, rate of dissolution, bioavailability, Cmax, Tmax, physicochemical stability, down-stream processibility (e.g. flowability compressibility, degree of brittleness, particle size manipulation), decrease in polymorphic form diversity, toxicity, taste, production costs, and manufacturing methods.

In the development of orally delivered drugs, it is often advantageous to have novel crystal forms of such drugs that possess improved properties, including increased aqueous solubility and stability. In many cases, the dissolution rate increase of drugs is desired as it would potentially increase their bioavailability. This also applies to the development of novel forms of zoledronic acid which, when administered orally to a subject, could achieve a greater or similar bioavailability and PK profile when compared to an IV or other formulations on a dose-for-dose basis.

Cocrystals, salts, solvates and hydrates of zoledronic acid of the present invention could give rise to improved properties of zoledronic acid. For example, a new form of zoledronic acid is particularly advantageous if it can improve the bioavailability of orally delivered zoledronic acid. Of particular interest are molecular complexes the zoledronic acid and the standard amino acids such as lysine. A schematic diagram for zoledronic acid:lysine complex is shown below. The diagram shows a molecular structure of the complex and possible interactions between the constituents of the complex which is different from the physical mix of the constituents.

Zoledronic acid: lysine complex

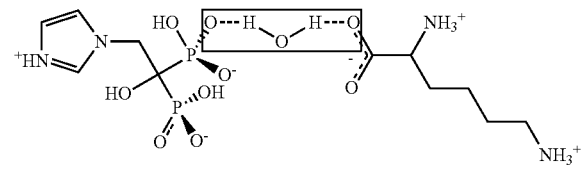

These represent one of the arrangements that molecules of the drug and the standard amino acids coformers could interact to form a stable complex that even when stressed thermally at elevated relative humidity (RH) environment have not displayed any signs of deterioration or disintegration to its original constituents. Such stability can be attributed to the hydrogen bonding (dashed line in the box) in these molecular complexes. When packing in a crystal structure these complexes have very different morphologies to that of its constituents or their physical mix as indicated by their powder X-ray diffraction (PXRD) patterns and therefore would possess different, unpredictable physicochemical properties.

The present invention provides a new crystal form of zoledronic acid in the form of a zoledronic DL-lysine complex (Form S), characterized by an PXRD pattern having strong peaks at about 7.2, 14.0, 18.3, 19.1, 20.7, 24.6 and 34.4±0.2 degrees two-theta.

The present invention provides a new crystal form of zoledronic acid in the form a zoledronic acid DL-lysine complex (Form T), characterized by a PXRD pattern having strong peaks at about T=6.6, 11.0, 14.2, 18.3, 19.7, 22.7, 27.6±0.2 degrees two-theta.

Accordingly, in a first aspect, the present invention includes complexes of zoledronic acid DL-lysine, which are capable of complexing in the solid-state, for example, through dry or solvent-drop grinding (liquid assisted grinding), heating or solvent evaporation of their solution in single or mixed solvent systems, slurry suspension, supercritical fluids or other techniques known to a person skilled in the art.

Another aspect of the invention provides novel complexes of zoledronic acid and DL-lysine that have been observed by their PXRD patterns which are different from all the previous molecular complexes prepared.

Another aspect of the invention provides complexes of zoledronic acid and DL-lysine, suitable for a pharmaceutical formulation than can be delivered orally to the human body. The pharmaceutical formulation contains a therapeutically effective amount of at least one of the novel molecular complexes of zoledronic acid according to the invention and at least one pharmaceutically acceptable carrier, (also known in the art as a pharmaceutically acceptable excipient). The novel molecular complexes of zoledronic acid are therapeutically useful for the treatment and/or prevention of disease states associated with osteoporosis, hypercalcemia (TIH), cancer induced bone metastasis, Paget's disease or adjuvant or neo-adjuvant therapies discussed above.

The invention also relates to methods of treatment using novel molecular complexes of zoledronic acid of the invention or a pharmaceutical formulation containing them. A pharmaceutical formulation of the invention may be in any pharmaceutical form which contains a novel molecular complex of zoledronic acid according to the invention. The pharmaceutical formulation may be, for example, a tablet, capsule, liquid suspension, injectable, suppository, topical, or transdermal. The pharmaceutical formulations generally contain about 1% to about 99% by weight of at least one novel molecular complex of zoledronic acid of the invention and 99% to 1% by weight of a suitable pharmaceutical excipient.

Another aspect of the invention provides the addition of excess cocrystal formers to the zoledronic acid complexes.

Another aspect of the invention provides a method where the excess cocrystal formers consist of standard amino acids.

The techniques and approaches set forth in the present disclosure can further be used by the person of ordinary skill in the art to prepare variants thereof, said variants are considered to be part of the inventive disclosure.

EXAMPLES

The following examples illustrate the invention without intending to limit the scope of the invention.

Zoledronic acid as a starting material used in all experiments in this disclosure was supplied by Farmkemi Limited (Wuhan Pharma Chemical Co.), China with purity of ca. 98% and was purified further via recrystallization from water. All other pure chemicals (Analytical Grade) were supplied by Sigma-Aldrich and Fisher and used without further purification.

Solid Phase Characterization

Analytical techniques used to observe the crystalline forms include PXRD. The particular methodology used in such analytical techniques should be viewed as illustrative, and not limiting in the context of data collection. For example, the particular instrumentation used to collect data may vary; routine operator error or calibration standards may vary; sample preparation method may vary.

Powder X-Ray Diffraction (PXRD): All zoledronic acid molecular complex products were observed by a D-8 Bruker X-ray Powder Diffractometer using Cu Kα ($\lambda$=1.540562 Å), 40 kV, 40 mA. The data were collected over an angular range of 3° to 45° 2θ in continuous scan mode at room temperature using a step size of 0.03 and 0.05° 2θ and a scan speed of 6.17°/min.

Example 1

Preparation of Zoledronic Acid (ZA) DL-Lysine Complex Form S Methods

A. Approximately 20-30 mg of Zoledronic acid (ZA) DL-lysine water molecular complex prepared as in previous applications; Example 12 in PCT U.S. Pat. No. 1,123,427 and in Example 13 in U.S. application Ser. No. 12/847,568 was dissolved in acetic acid (0.6 mL) at 90° C. in a 7-mL glass vial. The hot solution was polish-filtered through a syringe filter to a clean pre-heated vial. Anti-solvent was added until the solution turned turbid. The resulting hot solution was stored in a refrigerator (4° C.) for 15 hours to achieve a rapid cooling and induce particle formation. The particulate material was isolated by filtration and dried at ambient temperature under vacuum (30 in Hg) for 15 hours. This novel form can be obtained using a variety of anti-solvents such as dioxane, N-methylpyrrolidone (NMP), dimethylformamide (DMF) and dimethylacetamide (DMA).

B. Approximately 20-30 mg of ZA:DL-Lysine water complex prepared as in previous applications; Example 12 in PCT U.S. Pat. No. 1,123,427 and in Example 13 in U.S. application Ser. No. 12/847,568 was dissolved in acetic acid (0.6 mL) at 90° C. in a 7-mL glass vial. The hot solution was polish-filtered through a syringe filter to a clean pre-heated vial. Anti-solvent was added until the solution turned turbid. The resulting hot solution was stirred with a magnetic stir bar and cooled to room temperature at 20° C./h. The mixture was stirred at room temperature for approximately 15 hours and solid precipitates were isolated by filtration and were dried at ambient temperature under vacuum (30 in Hg) for 15 hours. The PXRD patterns of the solids were consistent with the patterns obtained from method A. This novel form can be also obtained using dimethylsulfoxide (DMSO), DMF and DMA as anti-solvents.

C. Approximately 26 mg of ZA:DL Lysine water complex prepared as in previous applications; Example 12 in PCT U.S. Pat. No. 1,123,427 and in Example 13 in U.S. application Ser. No. 12/847,568 was partially dissolved in acetic acid (10 mL) at 70° C. in a 20-mL glass vial. The hot mixture was polish-filtered through a syringe filter to a clean pre-heated vial. Diethoxymethane (10 mL) was added as an anti-solvent to give a turbid solution. The resulting hot solution was stirred for 15 hours with a magnetic stir bar and cooled to room temperature at 20° C./h to induce particle formation. The solid precipitates were isolated by filtration and dried at ambient temperature under vacuum (30 in Hg) for 15 hours and its PXRD pattern of the solids was consistent with the patterns obtained from methods A and B.

Example 2

Preparation of Zoledronic Acid DL-Lysine Complex Form T Methods

A. Approximately 20-30 mg of ZA:DL-Lysine water complex prepared as in previous applications; Example 12 in PCT U.S. Pat. No. 1,123,427 and in Example 13 in U.S. application Ser. No. 12/847,568 was dissolved in acetic acid (0.6 mL) at 90° C. in a 7-mL glass vial. The hot solution was polish-filtered through a syringe filter to a clean pre-heated vial. Anti-solvent was added until the solution turned turbid. The resulting hot solution was stored in a refrigerator (4° C.) for to 15 hours to achieve a rapid cooling and induce further particle formation. The solid particulate material were isolated by filtration and dried at ambient temperature under vacuum (30 in Hg) for 15 hours. The PXRD pattern was different from that generated by example 1. This novel form can be obtained using a variety of anti-solvents such as Toluene, butylacetate (BuOAc) and MIBK.

B. Approximately 20-30 mg of ZA:DL-Lysine water complex prepared as in previous applications; Example 12 in PCT U.S. Pat. No. 1,123,427 and in Example 13 in U.S. application Ser. No. 12/847,568 was dissolved in acetic acid (0.6 mL) at 90° C. in a 7-mL glass vial. The hot solution was polish-filtered through a syringe filter to a clean pre-heated vial. Anti-solvent was added until the solution turned turbid. The resulting slurry was stirred with a magnetic stirrer bar for 15 hours and cooled to room temperature at 20° C./h to affect precipitation. The precipitates were isolated by filtration and dried at ambient temperature under vacuum (30 in Hg) for 15 hours and PXRD patterns of the solids were consistent with that obtained from method A. This novel form can also be obtained using a variety of anti-solvents such as Toluene, BuOAc and NMP.

C. Approximately 20-30 mg of ZA:DL-Lysine water complex prepared as in previous applications; Example 12 in PCT U.S. Pat. No. 1,123,427 and in Example 13 in U.S. application Ser. No. 12/847,568 was partially dissolved in acetic acid (10 mL) at 70° C. in a 20-mL glass vial. The hot solution was polish-filtered through a syringe filter to a clean pre-heated vial. Anti-solvent was added until the solution became turbid. The resulting solution was stored in a refrigerator (4° C.) for 15 hours to achieve a rapid cooling and induce particle formation. The solid precipitates were isolated by filtration and were dried at ambient temperature under vacuum (30 in Hg) for 15 hours. The PXRD patterns of the solids were consistent with that obtained from methods A and B. This novel form can also be obtained using a variety of anti-solvents such as ethanol, ethylacetate (EtOAc), isopropanol (IPA), isopropylacetate (IPAc), and diethoxymethane (DEM).

D. Approximately 20-30 mg of ZA:DL-Lysine water complex prepared as in previous applications; Example 12 in PCT U.S. Pat. No. 1,123,427 and in Example 13 in U.S. application Ser. No. 12/847,568 was partially dissolved in acetic acid (10 mL) at 70° C. in a 20-mL glass vial. The hot solution was polish-filtered through a syringe filter to a clean pre-heated vial. Anti-solvent heptane was added until the solution turned turbid. The resulting hot solurry was stirred with a magnetic stir bar for 15 hours and cooled to room temperature at 20° C./h to enhance particle formation. The particulate material was then isolated by filtration and dried at ambient temperature under vacuum (30 in Hg) for 15 hours. The PXRD pattern was consistent with that obtained from methods A, B and C.

E. 31.7 mg of ZA:DL-Lysine water complex prepared as in previous applications; Example 12 in PCT U.S. Pat. No. 1,123,427 and in Example 13 in U.S. application Ser. No. 12/847,568 was dissolved in acetic acid (0.6 mL) at 90° C. and stirred with a magnetic stir bar. After 30 minutes of stirring the solution turned turbid and a precipitate was observed. The solids were isolated by filtration upon cooling to room temperature at 20° C./h. PXRD pattern of the material was consistent with that obtained from methods A, B, C and D.

F. Approximately 100 mg of ZA:DL-Lysine water complex prepared as in previous applications; Example 12 in PCT U.S. Pat. No. 1,123,427 and in Example 13 in U.S. application Ser. No. 12/847,568 was slurried in acetic acid (20 mL) at 70° C. and stirred for 30 minutes. The mixture was cooled to room temperature under ambient conditions and filtered to isolate particulate material. PXRD pattern of the isolated particles was consistent with that obtained from methods A, B, C, D and E.

Example 3

Scale Up of Zoledronic Acid DL-lysine Complex Form T Using Method B of Example 2

Figure 2:
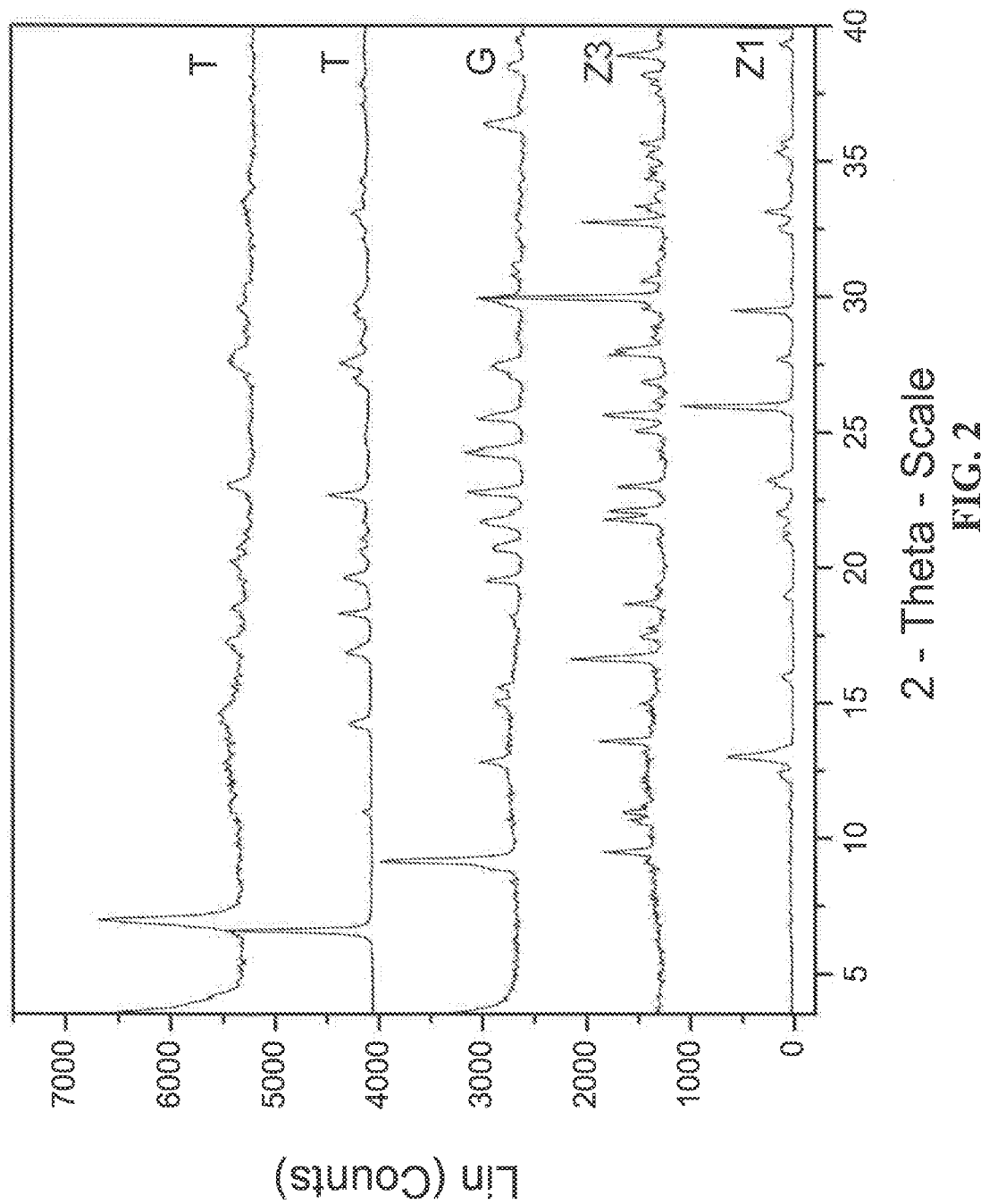
FIG. 2 PXRD diffractograms of: (T=zoledronic:DL-lysine complex scaled up, T=zoledronic:DL-lysine complex, (G=DL-lysine), (Z1=Zoledronic acid monohydrate), and (Z3=Zoledronic acid trihydrate).

Approximately 15 mL of acetic acid was added to 500 mg of ZA:DL-Lysine water complex prepared as in previous applications; Example 12 in PCT U.S. Pat. No. 1,123,427 and in Example 13 in U.S. application Ser. No. 12/847,568 to make a slurry. The slurry was heated while stirring until most of the solids were dissolved. The solution was filtered to remove the remaining solids. 2 mL of toluene was then added to the filtrate while stirring. The resulting suspension was heated and an additional 8 mL of acetic acid was added. After ca. 5 minutes the suspension was removed from heat and left to stir for 18 hours allowing the suspension to cool to room temperature. The particulate material was isolated and left under vacuum (22 in Hg) for 48 hrs. T was isolated in ca. 81% yield. The PXRD, of this product, the top profile in FIG. 2, shows a similar pattern to that obtained from Example 2 experiments.

This experiment demonstrates the ability to reproduce as well as scale up the process of generating the novel form T 20-fold. The variations on scale or method of preparation would be obvious to the person with ordinary skill in the art.

Example 4

Conversion of Form T to Form S

A sample of Form T was stored in closed screw cap vials under ambient conditions in the cupboard for approximately 11 months. The sample was tested after 11 months via powder X-ray diffraction (PXRD) and found to have converted from Form (T) to Form (S).

We claim:

1. A crystalline form of zoledronic acid: DL-lysine.

2. The crystalline form of claim 1, wherein said crystalline form is characterized by a powder X-ray diffraction pattern comprising powder X-ray diffraction peaks at about 6.6, 11.0, 14.2, 18.3, 19.7, 22.7 and 27.6 ±0.2 degrees 2-theta.

3. The crystalline form of claim 1, wherein said crystalline form is characterized by a powder X-ray diffraction pattern comprising powder X-ray diffraction peaks at about 7.2, 14.0, 18.3, 19.1, 20.7, 24.6 and 34.4 ±0.2 degrees 2-theta.

4. A composition comprising the crystalline form of claim 1.

5. A pharmaceutical composition comprising the crystalline form of claim 1 and at least one pharmaceutically acceptable carrier.

6. The pharmaceutical composition of claim 5 wherein the pharmaceutical composition is a solid oral composition.

7. The pharmaceutical composition of claim 6, wherein the solid oral composition is a tablet or capsule.

8. The pharmaceutical composition of claim 5, wherein the pharmaceutical composition is a unit dose.

9. A method of treating or preventing a disease for which zoledronic acid is indicated, said method comprising the step of administering to a patient in need thereof a therapeutically effective amount of a pharmaceutical composition of claim 5.

10. The method of claim 9, wherein said disease is selected from the group consisting of osteoporosis, hypercalcemia, cancer induced bone metastasis, Paget's disease, adjuvant cancer therapy and neoadjuvant cancer therapy.

11. The method of claim 10, wherein said hypercalcemia is tumor induced hypercalcemia (TIH).

12. The method of claim 10, wherein said disease is cancer induced bone metastasis.

13. A method of making the crystalline form of claim 1, comprising the steps of: dissolving a zoledronic acid : DL-lysine water complex in acetic acid; forming zoledronic acid: DL-lysine crystals; and purifying said zoledronic acid:DL-lysine crystals from said acetic acid.

14. The method of claim 13, wherein said method comprises the step of contacting said zoledronic acid, DL-lysine and acetic acid with an antisolvent.

15. The method of claim 14, wherein said antisolvent is selected from the group consisting of ethanol, ethylacetate (EtOAc), isopropanol (IPA), isopropylacetate (IPAc), diethoxymethane (DEM), Toluene, BuOAc, N-methylpyrrolidone (NMP) and a heptane.

16. The method of claim 14, wherein said antisolvent is selected from the group consisting of dimethylsulfoxide (DMSO), dioxane, NMP, dimethylformamide (DMF), dimethylacetamide (DMA), and DEM.

17. A composition comprising the crystalline form of claim 2.

18. A composition comprising the crystalline form of claim 3.

19. A pharmaceutical composition comprising the crystalline form of claim 2 and at least one pharmaceutically acceptable carrier.

20. A pharmaceutical composition comprising the crystalline form of claim 3 and at least one pharmaceutically acceptable carrier.

* * * * *